(12) United States Patent
Wu

(10) Patent No.: US 10,899,966 B2
(45) Date of Patent: Jan. 26, 2021

(54) SELF-ORIENTED MATERIAL, SELF-ORIENTED LIQUID CRYSTAL MATERIAL AND MANUFACTURING METHOD OF LIQUID CRYSTAL PANEL

(71) Applicant: SHENZHEN CHINA STAR OPTOELECTRONICS TECHNOLOGY CO., LTD., Guangdong (CN)

(72) Inventor: Ling Wu, Guangdong (CN)

(73) Assignee: SHENZHEN CHINA STAR OPTOELECTRONICS TECHNOLOGY CO., LTD., Guangdong (CN)

( * ) Notice: Subject to any disclaimer, the term of this patent is extended or adjusted under 35 U.S.C. 154(b) by 346 days.

(21) Appl. No.: 16/088,343

(22) PCT Filed: Aug. 30, 2018

(86) PCT No.: PCT/CN2018/103137
§ 371 (c)(1),
(2) Date: Sep. 25, 2018

(87) PCT Pub. No.: WO2019/148827
PCT Pub. Date: Aug. 8, 2019

(65) Prior Publication Data
US 2020/0165518 A1 May 28, 2020

(30) Foreign Application Priority Data
Jan. 30, 2018 (CN) .......................... 2018 1 0090180

(51) Int. Cl.
*C07C 229/38* (2006.01)
*C09K 19/38* (2006.01)
(Continued)

(52) U.S. Cl.
CPC ........ *C09K 19/3852* (2013.01); *C07C 229/34* (2013.01); *C07C 229/38* (2013.01);
(Continued)

(58) Field of Classification Search
CPC . C07C 229/38; C07C 229/34; C09K 19/3852; G02F 1/133788
(Continued)

(56) References Cited

U.S. PATENT DOCUMENTS 6,783,814 B2 * 8/2004 Swager .................. C08G 61/02
428/11
7,601,849 B1 * 10/2009 Jen ........................ C07D 333/20
549/59

FOREIGN PATENT DOCUMENTS

CN 106833677 6/2017
CN 107108457 8/2017
(Continued)

*Primary Examiner* — Christopher M Raabe
(74) *Attorney, Agent, or Firm* — Leong C. Lei

(57) ABSTRACT

The invention provides a self-oriented material, a self-oriented liquid crystal material and a manufacturing method of the liquid crystal panel. The self-oriented material provided by the invention can be used for carrying out alignment on liquid crystal molecules, and a polyimide alignment layer is not required to be arranged in the liquid crystal panel when the self-oriented material is added into the liquid crystal material. The self-oriented liquid crystal material disclosed by the invention contains the self-oriented material, the self-oriented material can be used for carrying out alignment on liquid crystal molecules, therefore a polyimide alignment layer is not required to be arranged in the liquid crystal panel. According to the manufacturing method of the liquid crystal panel, the orientation of the liquid crystal molecules is realized by utilizing the self-oriented material in the self-oriented liquid crystal material, and the polyimide alignment layer does not need to be manufactured, so that (Continued)

the process for manufacturing the polyimide alignment layer is saved, and the production cost is reduced.

8 Claims, 4 Drawing Sheets

(51) Int. Cl.
  *C07C 229/34* (2006.01)
  *C07C 237/20* (2006.01)
  *G02F 1/1337* (2006.01)
  *G02F 1/1341* (2006.01)
(52) U.S. Cl.
  CPC .......... *C07C 237/20* (2013.01); *G02F 1/1341* (2013.01); *G02F 1/133788* (2013.01); *G02F 2001/13415* (2013.01)
(58) Field of Classification Search
  USPC .......................................................... 445/6
  See application file for complete search history.

(56) References Cited

FOREIGN PATENT DOCUMENTS

| | | |
|---|---|---|
| CN | 107418598 | 12/2017 |
| CN | 108192643 | 6/2018 |
| JP | 2015125151 A | 7/2015 |
| KR | 20110031127 A * | 3/2011 |
| WO | 2017209161 | 12/2017 |

* cited by examiner

SELF-ORIENTED MATERIAL, SELF-ORIENTED LIQUID CRYSTAL MATERIAL AND MANUFACTURING METHOD OF LIQUID CRYSTAL PANEL

RELATED APPLICATIONS

The present application is a National Phase of International Application Number PCT/CN2018/103137, filed Aug. 30, 2018, and claims the priority of China Application No. 201810090180.5, filed Jan. 30, 2018.

BACKGROUND OF THE INVENTION

Field of the Invention

The present invention relates to the technical field of display, in particular to a self-oriented material, a self-oriented liquid crystal material and a manufacturing method of the liquid crystal panel.

Discussion of the Related Art

With the development of the display technology, the plane display device such as the liquid crystal display (LCD) has the advantages of being high in image quality, power saving, thin in the machine body, wide in application range and the like, and is widely applied to mobile phone, television, personal digital assistant and digital camera, notebook computers, desktop computers and the like, and becomes a mainstream in the display device.

The liquid crystal display device is formed by controlling the orientation of liquid crystal molecules with birefringence, which control the light transmission/disconnection (displayed on/off). The liquid crystal display device includes an upper substrate and a lower substrate which are arranged in parallel, and a liquid crystal medium mixture filled between the upper substrate and the lower substrate. A polymer layer is further arranged on the surface of the liquid crystal layer side of the upper substrate and the lower substrate, and is mainly used for controlling the orientation of the liquid crystal molecules. The polymer layer is generally referred to as an alignment layer (often adopting a polyimide material).

In the liquid crystal display, the orientation layer is used so that the orientation of the liquid crystal molecules can be well controlled, and the LCD (liquid crystal display) on/off is realized in a power-on/power-off process. But the polyimide material has the following disadvantages: Firstly, polyimide material and the polyimide material have high water absorption, so the storage condition is relatively tight, and is easy to go bad during the transportation process. The requirement for the transportation condition is high, and the transportation cost is high. Secondly, the polyimide material is relatively expensive. Thirdly, the solvent of the polyimide material uses n-methyl pyrrolidone (NMP), which is not environment-friendly and is easy to cause harm to a human body. Fourthly, in the manufacturing process of the liquid crystal display, the film forming process of the polyimide material is relatively complicated, and the relevant equipment is high in price, Fifthly, the polyimide material applied to a display panel has a certain requirement on the use temperature, which limits the development with other materials. Sixthly, when the polyimide alignment layer has poor coating uniformity, not sticky, or existing foreign bodies and the like, the product yield is affected and the product cost is increased. Therefore, in the manufacturing process of the TFT-LCD, if the manufacturing steps of the polyimide alignment layer can be omitted., the damage to the environment and people can be reduced, and the cost can be greatly saved.

SUMMARY

The present invention aims to provide a self-oriented material which can be used for aligning liquid crystal molecules. When the self-oriented material is added into the liquid crystal material, a polyimide alignment layer does not need to he arranged in the liquid crystal panel.

The present invention aims to provide a self-oriented liquid crystal material which contains the self-oriented material. The self-oriented material can be used for carrying out alignment on liquid crystal molecules, so that the polyimide alignment layer does not need to be arranged in the liquid crystal panel.

The present invention further provides a manufacturing method of the liquid crystal panel, and the orientation of the liquid crystal molecules is realized by utilizing the self-oriented material in the self-oriented liquid crystal material, and the polyimide alignment layer does not need to be manufactured.

In order to achieve the aim, the invention provides a self-oriented material which includes one or more of a compound conforming to the general formula (I).

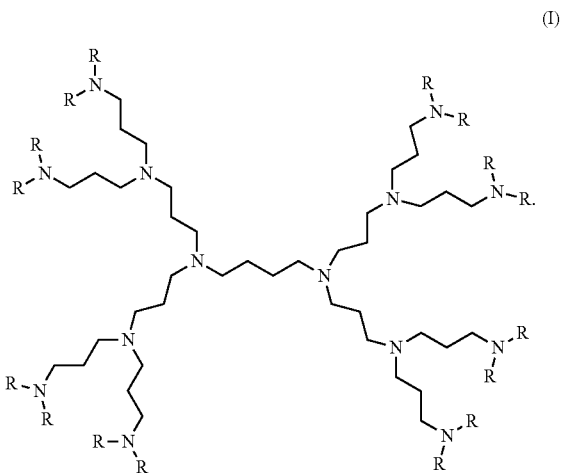

(I)

Wherein the part except sixteen R groups in the general formula is defined as a dendritic structure body, wherein the sixteen R groups are selected from one or two of the following general formula (II) and the general formula (III).

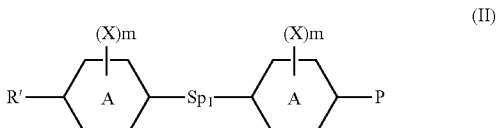

(II)

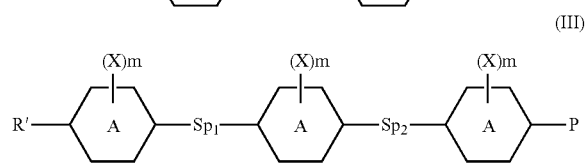

(III)

Wherein the plural

in the structural general formula (II) and the general formula (III) are aromatic rings or cycloalkanes.

Wherein the SP1 and SP2 are chemical bonds, —(CH$_2$)$_n$ or —(CH$_2$)$_n$—O—; n is an integer from 1 to 6 in the —(CH$_2$)$_n$ or —(CH$_2$)$_n$—O, wherein one or more of the —(CH$_2$)— can be substituted with —O—, —S—, —CO—, —CO—O—, —O—CO—, —O—CO—O—, —OCH$_2$—, —CH$_2$O—, —CH=CH—, —CF=CF—, or —C≡C—.

Wherein the P is an alkyl group with 3 –8 C atoms connected with a polymerizable group at the tail end, wherein one or more —CH$_2$— of the alkyl groups can be substituted with —O—, —CONH—, —COO—, —O—CO—, —CO—, or —CH=CH— group, one or more H atoms in the alkyl group can be replaced by F or CL atoms.

Wherein the X is a substituted group selected from —F, —Cl, —Br, —CH$_3$, —CN, and an alkyl group with 2 –8 C atoms; one or more non-adjacent —CH$_2$— in the alkyl group can be replaced by —o— or —s—. The m is the number of the substituent groups X connected to the same

The m is an integer from 0 to 4.

Wherein the R' is a hydrogen atom or an alkyl or alkenyl group having 1 –8 C atoms, wherein the alkyl group and the alkenyl group are in a straight chain shape.

Wherein the R selected from the structural general formula (II) or the structural general formula (III) is connected with the dendritic structure main body in the general formula (I) through the tail end of the P group.

Wherein the aromatic ring includes a benzene ring, and the SP1 and the SP2 are the same or different. The polymerizable group at the tail end of the P group includes one of a methacrylate group, an acrylic ester group, a vinyl group and an ethylencoxy group.

Wherein sixteen R groups of the general formula (I) are selected from one or more of the following structural formulas:

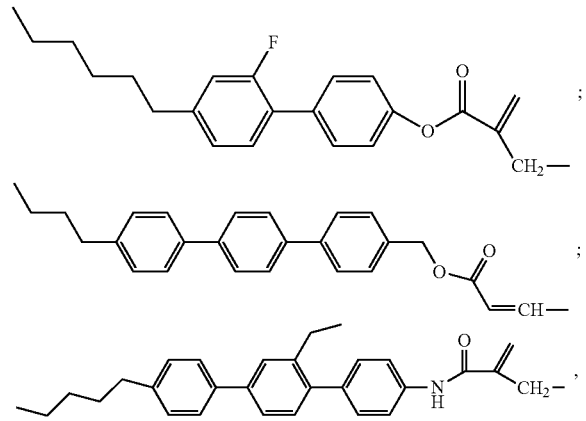

In another aspect, the present provides a self-oriented liquid crystal material including a liquid crystal material and the self-oriented material, wherein the liquid crystal material includes liquid crystal molecules.

Wherein the mass percent of the self-oriented material in the self-oriented liquid crystal material is 0.1%-2%.

In another aspect, the present provides a manufacturing method of the liquid crystal panel comprising the following steps of providing a first substrate, a second substrate and the self-oriented liquid crystal material; dripping or ink-jet printing the self-oriented liquid crystal material on the first substrate or the second substrate, and attaching the first base plate and the second base plate to each other in a aligned manner.

The self-oriented liquid crystal material between the first substrate and the second substrate forms a liquid crystal layer, the self-oriented material in the liquid crystal layer is adsorbed on the surface of the first substrate and the surface of the second substrate by virtue of the dendritic structure body, and the self-oriented material is perpendicular to the surface of the first substrate and the surface of the second substrate, so that the liquid crystal molecules is guided to be perpendicular to the first substrate and the second substrate.

The voltage is applied to the two sides of the liquid crystal layer, so that the liquid crystal molecules being deflected. The ultraviolet irradiation is carried out on the liquid crystal layer while voltage is applied. The self-oriented material is subjected to polymerization reaction, and forms a first polymer layer and a second polymer layer on the surface of the first substrate and the surface of the second substrate respectively.

The voltage is removed on the two sides of the liquid crystal layer, and under the action of the first polymer layer and the second polymer layer, the liquid crystal molecules in the liquid crystal layer generates a pre-inclination angle.

Wherein the first electrode is arranged on the first substrate, and a second electrode is arranged on the second substrate. When the first substrate is in alignment fit with the second substrate, the first electrode is arranged towards the second substrate, and the second electrode is arranged towards the first substrate. The voltage is formed between the first electrode and the second electrode, and therefore voltage is applied to the two sides of the liquid crystal layer.

Wherein the manufacturing method further includes steps of coating frame glue and curing frame glue. The step of coating frame glue occurs before the alignment of the first substrate and the second substrate is carried out. The step of coating frame glue includes coating a frame glue on the periphery of the second substrate or the first substrate corresponding to the self-oriented liquid crystal material. The step of curing the frame glue occurs before the voltage is applied to the two sides of the liquid crystal layer, and the step of curing the frame glue includes at least one of UV curing and thermal curing.

The self-oriented material disclosed by the invention has the beneficial effects that the self-oriented material can be used for carrying out alignment on liquid crystal molecules, when the self-oriented material is added into the liquid crystal material, the polyimide alignment layer does not need to be arranged in the liquid crystal panel. The self-oriented liquid crystal material contains the self-oriented material, and the self-oriented material can be used for carrying out alignment on liquid crystal molecules, so that the polyimide alignment layer does not need to be arranged in the liquid crystal panel. According to the liquid crystal panel manufacturing method of the present invention, the orientation of the liquid crystal molecules is realized by utilizing the self-oriented material in the self-oriented liquid crystal material, and the polyimide alignment layer does not need to be manufactured. So the process for manufacturing the polyimide alignment layer is saved, the production cost is reduced, and the alignment effect of the liquid crystal molecules is good.

In order to better understand the features and technical contents of the present invention, please refer to the following detailed description and the accompanying drawings of the present invention. The drawings are not necessarily to scale the present invention, but the emphasis instead being placed upon clearly illustrating the principles of the present disclosure.

BRIEF DESCRIPTION OF THE DRAWINGS

The specific embodiments of the present invention are described in detail with reference to the accompanying drawings, which clearly shows the technical scheme of the invention and other beneficial effects are obvious.

In the drawings.

DETAILED DESCRIPTION OF THE EMBODIMENTS

In order to further expel the technical means adopted by the present invention and the effect thereof, the present invention is described in detail with reference to preferred embodiments of the present invention and the accompanying drawings.

Figure 2:
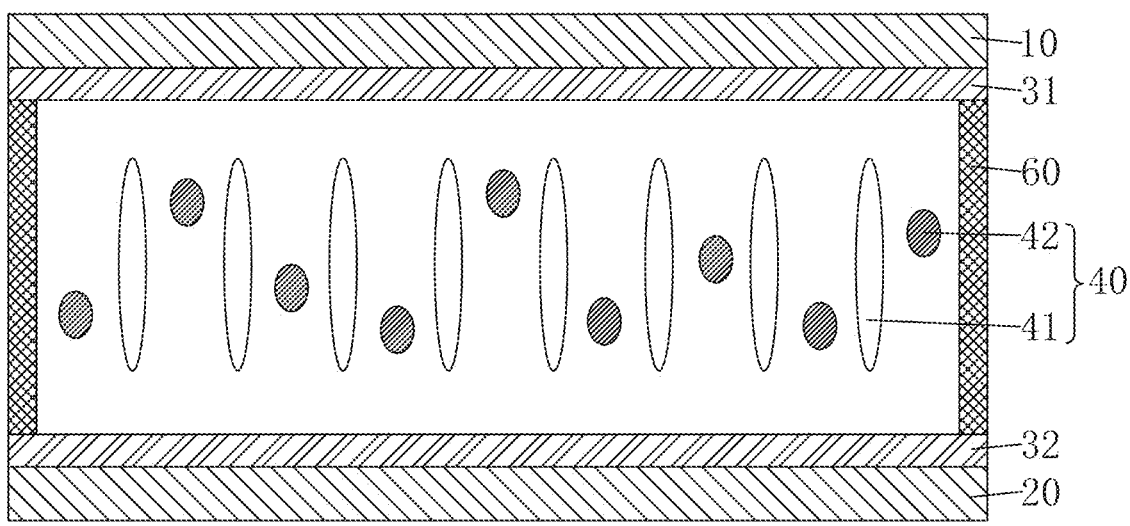
FIG. 2 is a schematic diagram of a step S2 of a manufacturing method of a liquid crystal panel according to the invention.

Referring to FIG. 2, a self-oriented material 42 is provided, which includes one or more of compounds conforming to the following structural general formula (I):

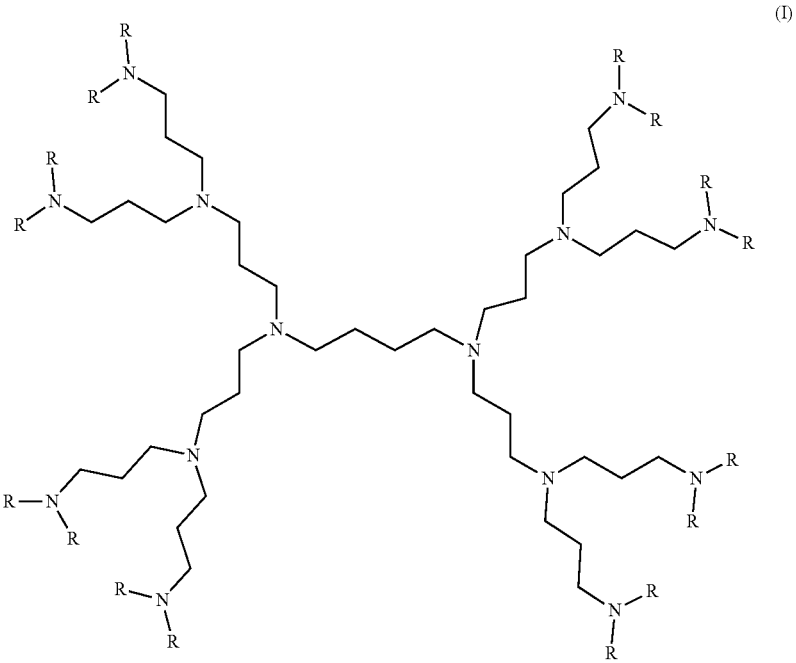

(I)

The part except sixteen R groups in the structural general formula is defined as a dendritic structure body.

The sixteen R groups are selected from one or two of the structural following general formula (II) and the general formula (III):

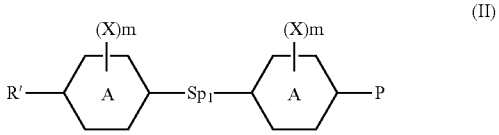

(II)

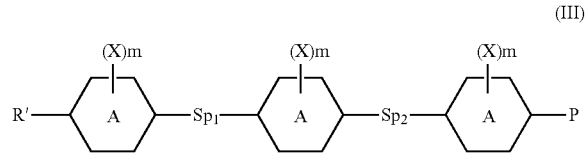

(III)

In the structural general formula (II) and the structural general formula (III),

are aromatic rings or cycloalkanes.

Specifically, the aromatic ring includes a benzene ring.

SP1 and SP2 are chemical bonds —(CH$_2$)$_n$ or —(CH$_2$)$_n$—O— n is an integer from 1 to 6 in the —(CH$_2$)$_n$ or —(CH$_2$)$_n$—O, wherein one or more of the —(CH$_2$)— can be replaced with —O—, —S—, —CO—, —CO—O—, —O—CO—O—, —O—CO—O—, —OCH$_2$—, —CH$_2$O—, —CH═CH—, —CF═CF—, or —C≡C—.

Specifically, the SP1 and the SP2 can be the same or different.

P is an alkyl group with 3 –8 C atoms connected with a polymerizable group at the tail end. The alkyl group is in a straight chain shape or a branched chain shape. One or more —CH$_2$— of the alkyl groups can be substituted with —O—, —CONH—, —COO—, —O—CO—, —CO—, or —CH═CH— group. One or more H atoms in the alkyl group can be replaced by F or CL atoms.

Specifically, the polymerizable group at the tail end of the P group includes one of the methacrylate group, the acrylic ester group, the vinyl group and the ethyleneoxy group.

X is a substituted group selected from —F, —Cl, —Br, —CH$_3$, —CN, and an alkyl group with two to eight C atoms. The alkyl group is in a straight chain shape or a branched chain shape. One or more non-adjacent —CH$_2$— in the alkyl group can be replaced by —O— or —S—. The m is the number of the substituent groups X connected to the same

and m is an integer from zero to four.

Specifically, when in is greater than 1, m substituent groups x can be the same or different.

R' is a hydrogen atom or an alkyl or alkenyl group having one to eight C atoms, and the alkyl group and the alkenyl group are in a straight chain shape.

R selected from the structural general formula (III) or the structural general formula (III) is connected with the dendritic structure main body in the general formula (I) through the tail end of the P group.

Specifically, the nitrogen (N) in the dendritic structure body of the self-oriented material 42 can form the hydrogen bond or intermolecular force between the atoms and the electrode layer on the surface of the substrate. The self-oriented material 42 is thus anchored to its surface. The plural nitrogen atoms are contained in the dendritic structure main body, so that a relatively strong interaction force can be formed with the surface of the substrate. Therefore, the self-oriented material 42 is firmly anchored on the surface of the substrate, and the alignment effect of the liquid crystal molecules is improved.

Specifically, in the structural general formula (II) and the structural general formula (III), the p group is a polymerizable group, and can be mutually polymerized under ultraviolet light irradiation, which lead to the self-oriented material 42 be cross-linked to form a polymer. The R' group is a flexible tail chain, and the group

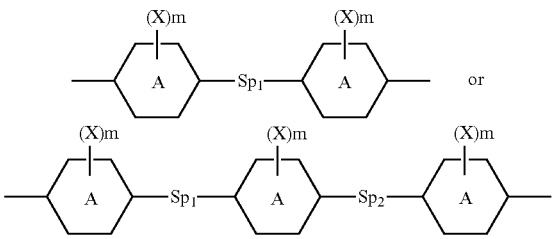

which is located between the P group and the R' group is a rigid group. In the alignment process of the liquid crystal molecules 41, the R' group with flexible tail chain and the rigid group connected with the R' group of the flexible tail chain are used for guiding the arrangement of the liquid crystal molecules 41.

Preferably, sixteen R groups in the structure general formula are selected from one or more of the following structural formulas,

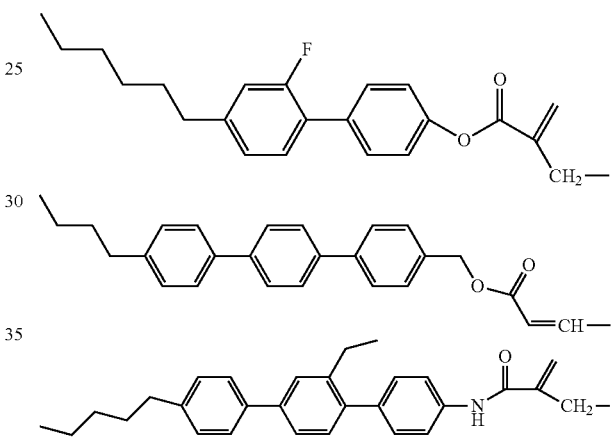

The self-oriented material 42 can be used for aligning the liquid crystal molecules 41, and when the self-oriented material 42 is added into the liquid crystal material, the polyimide alignment layer is not required to he arranged in a liquid crystal panel. Therefore, the process for manufacturing the polyimide alignment layer can be saved, the production cost is reduced, and the alignment effect of the liquid crystal molecules 41 is better.

Based on the self-oriented material 42, the present invention further provides a self-oriented liquid crystal material including a liquid crystal material and the self-oriented material 42. The liquid crystal material includes liquid crystal molecules 41.

Specifically, the mass percent of the self-oriented material 42 in the self-oriented liquid crystal material is 0.1%-2%, preferably 0.4% or 1%.

Specifically, in the self-oriented liquid crystal material, the liquid crystal material and the self-oriented material 42 are uniformly mixed so as to ensure that when the self-oriented liquid crystal material is irradiated by ultraviolet light, the self-oriented material 42 is polymerized to form a thin film with a uniform thickness in the process of manufacturing the liquid crystal panel.

The self-oriented liquid crystal material contains the self-oriented material 42. The self-oriented material 42 can be used for carrying out alignment on the liquid crystal molecules 41, so that the polyimide alignment layer does not need to he arranged in the liquid crystal panel. The process for manufacturing the polyimide alignment layer is saved, the production cost is reduced, and the alignment effect of the liquid crystal molecules 41 is better.

Figure 1:
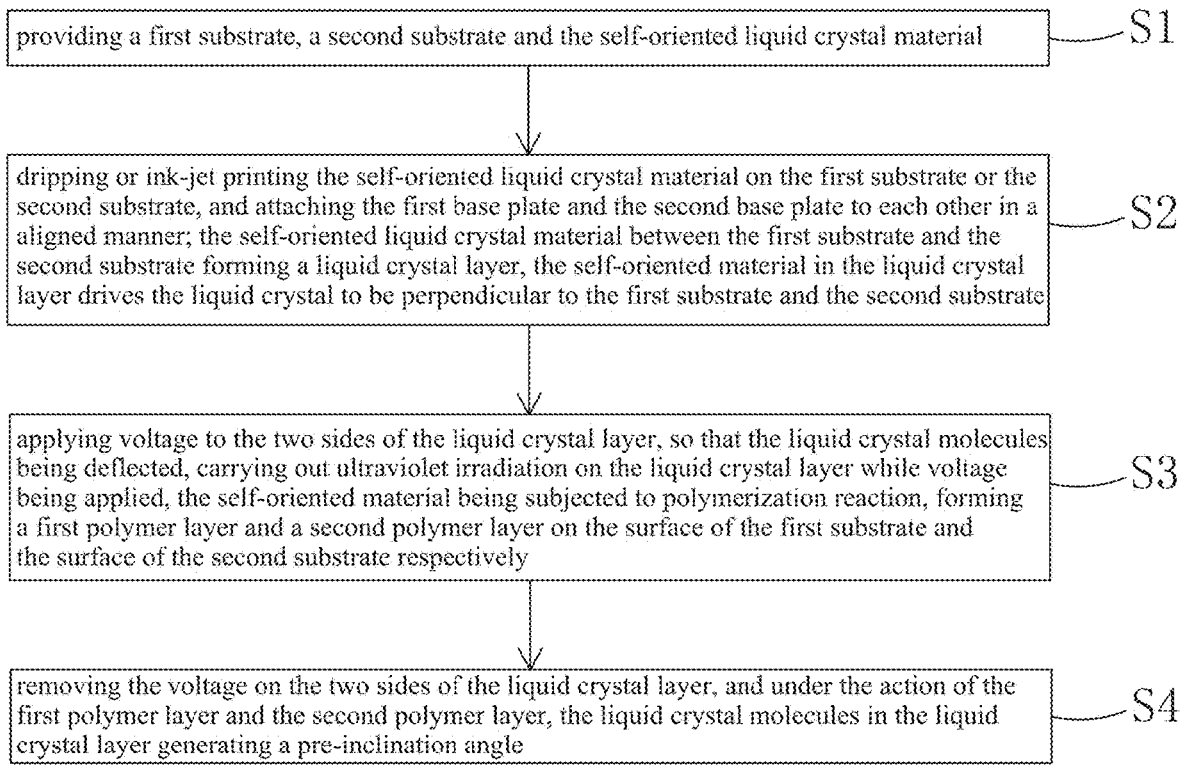
FIG. 1 is a flow chart of a manufacturing method of a liquid crystal panel according to the present invention.

Please refer to FIG. 1, based on the self-oriented liquid crystal material, the present invention further provides a manufacturing method of the liquid crystal panel. The manufacturing method includes the following steps.

In step S1, referring to FIG. 2, a first substrate 10, a second substrate 20 and the self-oriented liquid crystal material are provided.

Specifically, a first electrode 31 is arranged on the first substrate 10, and a second electrode 32 is arranged on the second substrate 20.

Specifically, the first substrate 10 and the second the substrate 20 is the color film substrate and the thin film transistor array substrate respectively. The first electrode 31 and the second electrode 32 are respectively the common electrode and the pixel electrode.

In step S2, please referring to FIG. 2, dripping or ink-jet printing (inkjet) the self-oriented liquid crystal material on the first substrate 10 or the second substrate 20 is used for aligning and laminating the first substrate 10 and the second substrate 20. The self-oriented liquid crystal material between the first substrate 10 and the second substrate 20 forms a liquid crystal layer 40. The self-oriented material 42 in the liquid crystal layer 40 is adsorbed on the surface of the first substrate 10 and the surface of the second substrate 20 through the dendritic structure body, and the self-oriented material 42 is perpendicular to the surface of the first substrate 10 and the surface of the second substrate 20, so that the liquid crystal molecules 41 are guided to be perpendicular to the first substrate 10 and the second substrate 20.

Preferably, a vacuum lamination process (VAS) is adopted for aligning the first substrate 10 with the second substrate 20.

Specifically, when the first substrate 10 and the second substrate 20 are aligned, the first electrode 31 is arranged towards the second substrate 20, and the second electrode 32 faces the first substrate 10.

Specifically, the one drop filling (ODF) process is adopted. The self-oriented liquid crystal material is dripped on the first substrate 10 or the second substrate 20.

Figure 3:
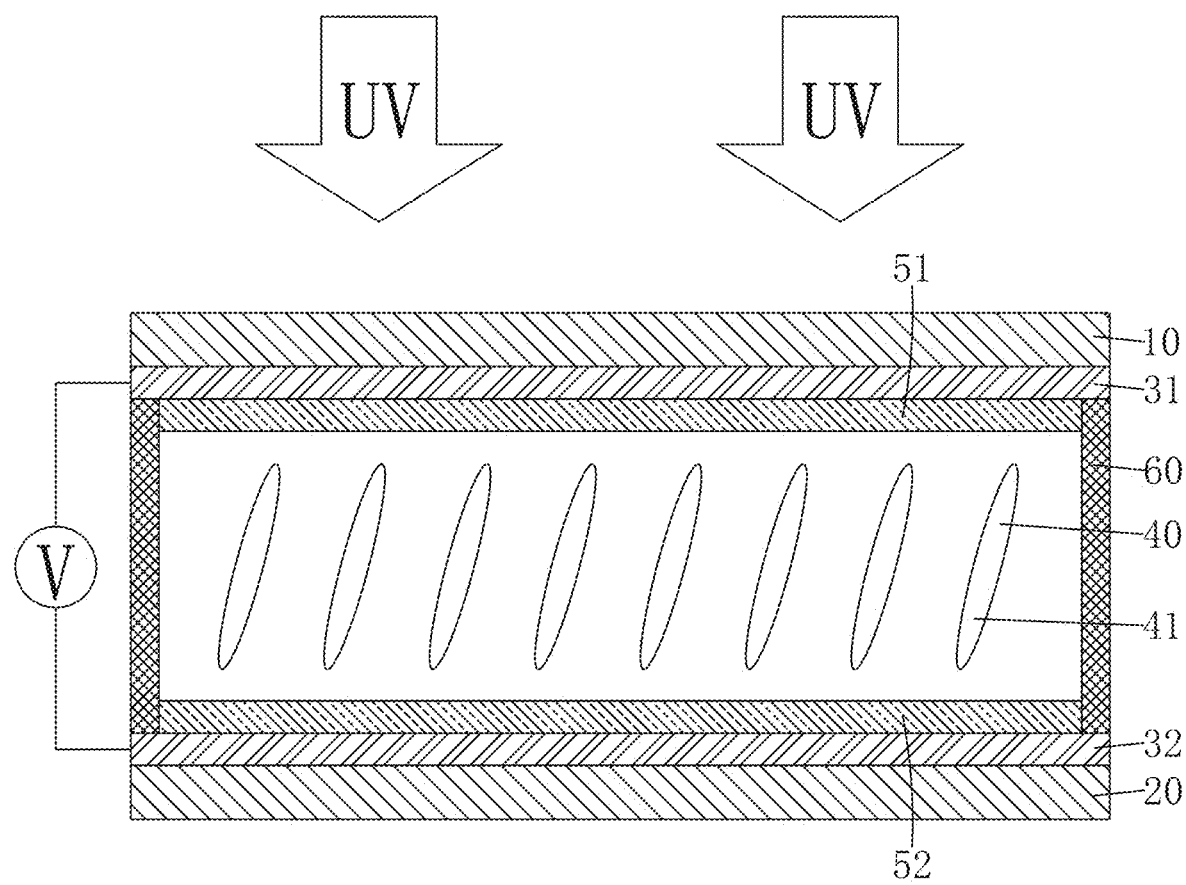
FIG. 3 is a schematic diagram of a step S3 of a manufacturing method of a liquid crystal panel according to the invention.

In step S3, referring to FIG. 3, voltages are applied to the two sides of the liquid crystal layer 40. After the liquid crystal molecules 41 are deflected, ultraviolet irradiation is carried out on the liquid crystal layer 40 while voltage is applied. The self-oriented material 42 has a polymerization reaction, and the first polymer layer 51 and the second polymer layer 52 are formed on the surfaces of the first substrate 10 and the second substrate 20 respectively.

Specifically, voltage is formed between the first electrode 31 and the second electrode 32, so that voltage is applied to the two sides of the liquid crystal layer 40.

Specifically, the liquid crystal material in the self-oriented liquid crystal material is uniformly mixed with the self-oriented material 42, so that the thickness of the film layer of the first polymer layer 51 and the thickness of the second polymer layer 52 formed by polymerizing the self-oriented material 42 is uniform.

Figure 4:
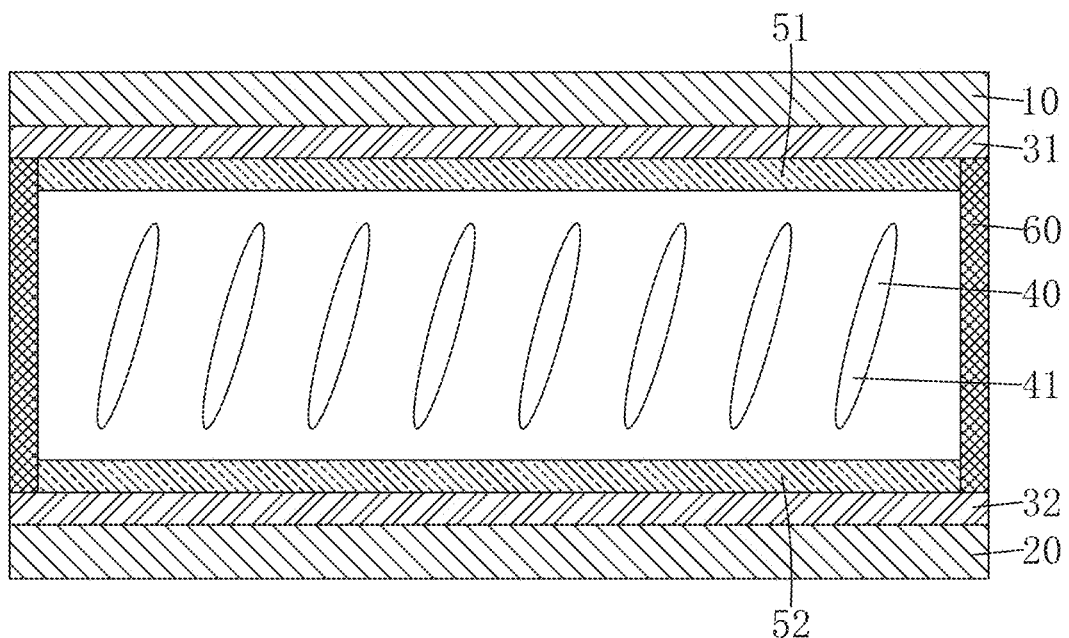
FIG. 4 is a schematic diagram of a step S4 of a method for manufacturing a liquid crystal panel according to the present invention and a structure diagram of the liquid crystal panel according to the present invention.

In step S4, referring to FIG. 4, voltages on the two sides of the liquid crystal layer 40 are removed. Under the action of the first polymer layer 51 and the second polymer layer 52, the liquid crystal molecules 41 in the liquid crystal layer 40 generate a pre-inclination angle.

Specifically, a plurality of protrusions (not shown) are arranged on the surfaces of the first polymer layer 51 and the second polymer layer 52, which are capable of maintaining the pre-inclination angle of the liquid crystal molecule 41 in the form of the space stereo banner.

Specifically, the manufacturing method of the liquid crystal panel further includes the steps of coating the frame glue 60 and curing the frame glue 60, The step of coating the frame glue 60 occurs before the alignment of the first substrate 10 and the second substrate 20. The step of coating frame glue 60 includes: coating the frame glue 60 on the second substrate 20 or the first substrate 10 corresponding to the periphery of the self-oriented liquid crystal material. The step of curing the frame glue 60 occurs before the voltage is applied to the two sides of the liquid crystal layer 40. The step of curing the frame glue 60 includes at least one of UV curing and thermal curing.

In a preferred embodiment of the self-oriented liquid crystal material, the liquid crystal material is a negative liquid crystal material, wherein the Tni is 74° C., the Δn is 0.0980 (25° C. and 589 nm), and Δε is −3.1 (25° C., and 1 kHz), Tni is a clear point temperature of the liquid crystal material, the Δn is the optical anisotropy of the liquid crystal material, and the Δε is the dielectric anisotropy of the liquid crystal material. The mass percent of the self-oriented material 42 in the self-oriented liquid crystal material is 1%. R groups in the structural general formula (I) of the self-oriented material 42 are

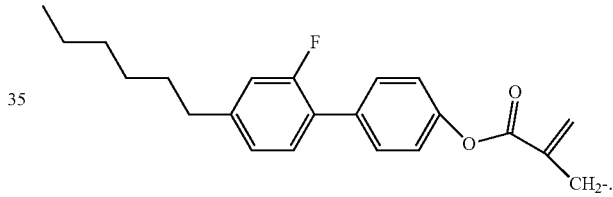

When the liquid crystal panel is manufactured by adopting the self-oriented liquid crystal material of the embodiment, the voltage applied to the two sides of the liquid crystal layer 40 is 13 v, and the frequency of the alternating current voltage is 4 Hz.

In another preferred embodiment of the self-oriented liquid crystal material of the present invention, the mass percent of the self-oriented material 42 in the self-oriented liquid crystal material is 0.4%. R groups in the structural general formula (I) of the self-oriented material 42 are

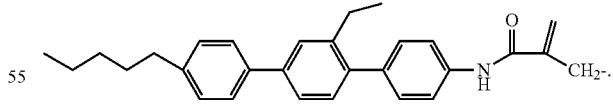

According to the manufacturing method of the liquid crystal panel, the orientation of the liquid crystal molecules 41 is realized by utilizing the self-oriented material 42 in the self-oriented liquid crystal material, and the polyimide alignment layer does not need to be manufactured. So that a process for manufacturing the polyimide alignment layer is saved, the production cost is reduced, and the alignment effect of the liquid crystal molecules 41 is better.

Referring to FIG. 4, the invention further provides a liquid crystal panel based on the manufacturing method of the liquid crystal panel, which includes a first substrate 10 and a second substrate 20 which are oppositely arranged, the first polymer layer 51 arranged on one side facing the second substrate 20 of the first substrate 10, the second polymer layer 52 arranged on one side facing the first substrate 10 of the second substrate 20, and the liquid crystal layer 40 arranged between the first polymer layer 51 and the second polymer layer 52. The liquid crystal layer 40 includes a liquid crystal material, and the liquid crystal material includes liquid crystal molecules 41, wherein the liquid crystal molecule 41 is provided with a pre-inclination angle.

The first polymer layer 51 and the second polymer layer 52 are fanned by polymerizing the self-oriented material 42.

Specifically, the liquid crystal panel further includes the frame 60, which is located between the first substrate 10 and the second substrate 20 and located on the periphery of the liquid crystal layer 40. The first electrode 31 is arranged between the first substrate 10 and the first polymer layer 51, and the second electrode 32 is arranged between the second substrate 20 and the second polymer layer 52

Specifically, the first substrate 10 and the second the substrate 20 are the color film substrate and the thin film transistor array substrate respectively. The first electrode 31 and the second electrode 32 are respectively a common electrode and a pixel electrode.

The liquid crystal panel realizes the alignment of the liquid crystal molecules 41 by utilizing the self-oriented material 42, and the polyimide alignment layer does not need to be arranged. The production cost is low, and the alignment effect of the liquid crystal molecules 41 is better.

In conclusion, the self-oriented material provided by the invention can be used for carrying out alignment on liquid crystal molecules. The self-oriented material is added into the liquid crystal material, and the polyimide alignment layer is not required to be arranged in the liquid crystal panel. The self-oriented liquid crystal material disclosed by the invention contains the self-oriented material, and the self-oriented material can be used for carrying out alignment on liquid crystal molecules. Therefore, the polyimide alignment layer is not required to be arranged in the liquid crystal panel. According to the manufacturing method of the liquid crystal panel in the present invention, the orientation of the liquid crystal molecules is realized by utilizing the self-oriented material in the self-oriented liquid crystal material, and the polyimide alignment layer does not need to be manufactured. So that a process for manufacturing the polyimide alignment layer is saved. The production cost is reduced, and the alignment effect of the liquid crystal molecules is better.

For the ordinary technical personnel in the field, other various corresponding changes and modifications can be made according to the technical scheme and technical ideas of the invention. All such changes and modifications shall fall within the protection scope of the claims of the present invention.

What is claimed is:

1. A self-oriented material, comprising one or more of a compound conforming to the general formula (I):

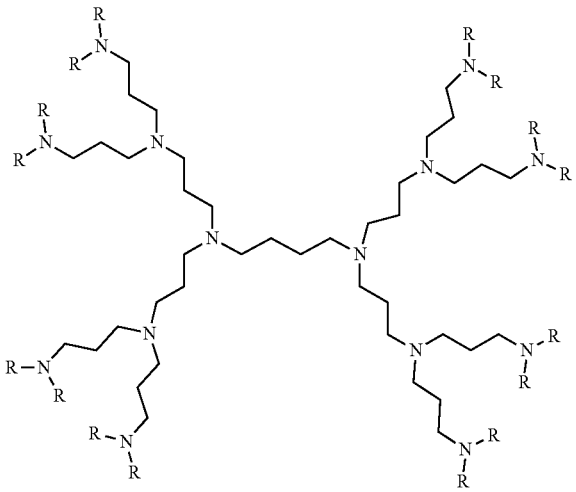

(I)

a part except sixteen R groups in the general formula is defined as a dendritic structure body; wherein the sixteen R groups are selected from one or two of the following general formula (II) and the general formula (III):

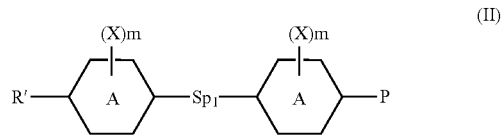

(II)

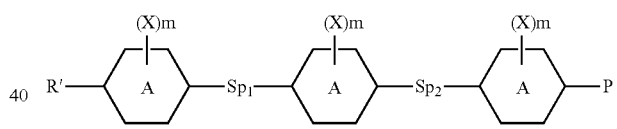

(III)

the plural

in the structural general formula (II) and the general formula (III) are aromatic rings or cycloalkanes;

SP1 and SP2 are chemical bonds, —$(CH_2)_n$— or —$(CH_2)_n$—O—; n is an integer from 1 to 6 in the —$(CH_2)_n$— or —$(CH_2)_n$—O, wherein one or more of the —$(CH_2)$— can be replaced with —O—, —S—, —CO—, —CO—O—, —O—CO—, —O—CO—O—, —OCH$_2$—, —CH$_2$O—, —CH=CH—, —CF=CF—, or —C≡C—;

P is an alkyl group with 3 -8 C atoms connected with a polymerizable group at the tail end, wherein one or more —CH$_2$— of the alkyl groups can be substituted with —O—, —CONH—, —COO—, —O—CO—, —CO—, or —CH=CH— group, one or more H atoms in the alkyl group can be replaced by F or CL atoms;

X is a substituted group selected from —F, —Cl, —Br, —CH$_3$, —CN, and an alkyl group with two to eight C atoms; one or more non-adjacent —CH$_2$— in the alkyl group can be replaced by —O— or —S—; m is the number of the substituent groups X connected to the same;

m is an integer from zero to four;
R' is a hydrogen atom or an alkyl or alkenyl group having one to eight C atoms, wherein the alkyl group and the alkenyl group are in a straight chain shape;
R selected from the structural general formula (II) or the structural general formula (III) is connected with the dendritic structure main body in the general formula (I) through the tail end of the P group.

2. The self-oriented material according to claim 1, wherein the aromatic ring comprises a benzene ring, and the SP1 and the SP2 are the same or different; wherein the polymerizable group at the tail end of the P group comprises one of a methacrylate group, an acrylic ester group, a vinyl group and an ethyleneoxy group.

3. The self-oriented material according to claim 1, wherein sixteen R groups of the general formula (I) are selected from one or more of the following structural formulas:

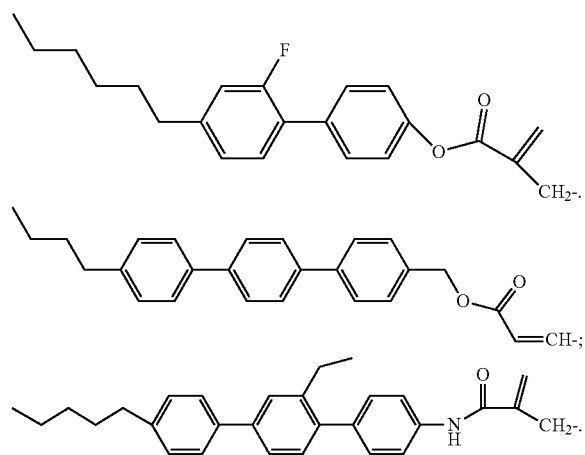

4. A self-oriented liquid crystal material, comprising a liquid crystal material and the self-oriented material as claimed in claim 1, wherein the liquid crystal material comprises liquid crystal molecules.

5. The self-oriented liquid crystal material according to claim 4, wherein the mass percent of the self-oriented material in the self-oriented liquid crystal material is 0.1%-2%.

6. A manufacturing method of the liquid crystal panel comprising the following steps:
providing a first substrate, a second substrate and the self-oriented liquid crystal material as claimed in claim 4;
dripping or ink-jet printing the self-oriented liquid crystal material on the first substrate or the second substrate, and attaching the first base plate and the second base plate to each other in a aligned manner; the self-oriented liquid crystal material between the first substrate and the second substrate forming a liquid crystal layer, the self-oriented material in the liquid crystal layer being adsorbed on the surface of the first substrate and the surface of the second substrate by virtue of the dendritic structure body, and the self-oriented material being perpendicular to the surface of the first substrate and the surface of the second substrate, so that the liquid crystal molecules being guided to be perpendicular to the first substrate and the second substrate;
applying voltage to the two sides of the liquid crystal layer, so that the liquid crystal molecules being deflected, carrying out ultraviolet irradiation on the liquid crystal layer while voltage being applied, the self-oriented material being subjected to polymerization reaction, forming a first polymer layer and a second polymer layer on the surface of the first substrate and the surface of the second substrate respectively;
removing the voltage on the two sides of the liquid crystal layer, and under the action of the first polymer layer and the second polymer layer, the liquid crystal molecules in the liquid crystal layer generating a pre-inclination angle.

7. The manufacturing method of the liquid crystal panel according to claim 6, wherein a first electrode is arranged on the first substrate, and a second electrode is arranged on the second substrate; when the first substrate is in alignment fit with the second substrate, the first electrode is arranged towards the second substrate, and the second electrode is arranged towards the first substrate; voltage is formed between the first electrode and the second electrode, and therefore voltage is applied to the two sides of the liquid crystal layer.

8. The manufacturing method of the liquid crystal panel according to claim 6, further comprising steps of coating frame glue and curing frame glue; and the step of coating frame glue occurs before the alignment of the first substrate and the second substrate is carried out, wherein the step of coating frame glue comprises: coating a frame glue on the periphery of the second substrate or the first substrate corresponding to the self-oriented liquid crystal material; the step of curing the frame glue occurs before the voltage is applied to the two sides of the liquid crystal layer, wherein the step of curing the frame glue comprises at least one of UV curing and thermal curing.

* * * * *